US012691156B2

(12) United States Patent
Lin et al.

(10) Patent No.: US 12,691,156 B2
(45) Date of Patent: Jul. 28, 2026

(54) **PREBIOTIC COMPOSITIONS AND METHOD FOR PROMOTING GROWTH OF *HAFNIA ALVEI* BY USING THE SAME**

(71) Applicant: TCI CO., LTD., Taipei (TW)

(72) Inventors: Yung-Hsiang Lin, Taipei (TW); Di Chang, Taipei (TW)

(73) Assignee: TCICO., LTD., Taipei (TW)

( * ) Notice: Subject to any disclaimer, the term of this patent is extended or adjusted under 35 U.S.C. 154(b) by 248 days.

(21) Appl. No.: 18/348,364

(22) Filed: Jul. 7, 2023

(65) Prior Publication Data

US 2024/0009261 A1     Jan. 11, 2024

Related U.S. Application Data

(60) Provisional application No. 63/359,204, filed on Jul. 8, 2022.

(51) Int. Cl.
| | |
|---|---|
| *A61K 36/82* | (2006.01) |
| *A61K 8/9789* | (2017.01) |
| *A61K 36/736* | (2006.01) |
| *A61K 38/04* | (2006.01) |
| *A61K 38/16* | (2006.01) |
| *A61P 3/04* | (2006.01) |
| *A61Q 19/08* | (2006.01) |

(52) U.S. Cl.
CPC ............ *A61K 36/82* (2013.01); *A61K 8/9789* (2017.08); *A61K 36/736* (2013.01); *A61K 38/04* (2013.01); *A61K 38/168* (2013.01); *A61P 3/04* (2018.01); *A61Q 19/08* (2013.01); *A61K 2236/17* (2013.01); *A61K 2236/19* (2013.01); *A61K 2800/522* (2013.01)

(58) Field of Classification Search
None
See application file for complete search history.

(56) References Cited

U.S. PATENT DOCUMENTS

2011/0123501 A1     5/2011   Chou et al.

FOREIGN PATENT DOCUMENTS

CN         111973504 A     11/2020

OTHER PUBLICATIONS

Asano (JP 2005187442 A—English translation)—Jul. 14, 2005.*
Lin (CN 111973504 A—English translation)—Nov. 24, 2020.*
Yue (CN 103689733 A—English translation)—Apr. 2, 2014.*
Jin-Rong Zhou et al., Dietary soy and tea combinations for prevention of breast and prostate cancers by targeting metabolic syndrome elements in mice, Am J Clin Nutr 2007; 86 (suppl): 882S-8S, American Society for Nutrition Abstract.
Marielle Malucelli Mallmann et al., Kombucha: A systematic review and meta-analysis of experimental evidence of its effects on blood glucose, dyslipidemia and body weight in diabetes mellitus, Society and Development, v. 11, n. 6, e49011629278, (CC by 4.0) ISSN 2525-3409, DOI: http://dx.doi.org/10.33448/rsd-v11i6.29278, May 5, 2022 Introduction , Table 2.

* cited by examiner

*Primary Examiner* — Susan Hoffman
(74) *Attorney, Agent, or Firm* — Chieh-Mei Wang

(57) ABSTRACT

A prebiotic composition includes a black tea ferment and a bioactive substance. The bioactive substance is soybean peptide powder, pea protein, rice protein, corn oligopeptide powder, or a combination thereof. The black tea ferment is prepared by the following steps: extracting tea leaves of *Camellia sinensis* with water at 50° C. to 100° C. for 0.5 hours to 3 hours to obtain a black tea extract, and fermenting the black tea extract with *Saccharomyces cerevisiae* BCRC20271, *Bifidobacterium lactis* BCRC910887, *Lactobacillus gasseri* BCRC910886, and *Gluconacetobacter xylinus* BCRC12335 for 12 days to 25 days to obtain the black tea ferment.

11 Claims, 6 Drawing Sheets

PREBIOTIC COMPOSITIONS AND METHOD FOR PROMOTING GROWTH OF *HAFNIA ALVEI* BY USING THE SAME

CROSS-REFERENCE TO RELATED APPLICATION

This application claims the benefit of U.S. provisional application Ser. No. 63/359,204, filed on Jul. 8, 2022. The entirety of the above-mentioned patent application is hereby incorporated by reference herein and made a part of the specification.

BACKGROUND

Technical Field

The present disclosure relates to a prebiotic composition and a method for weight loss by using the same. A black tea ferment and a bioactive substance are used for preparing the prebiotic composition, and the prebiotic composition is used for weight loss.

Related Art

Prebiotics, also known as GOS/FOS, are generally polysaccharides that are not easily digested by human enzymes in natural foods. According to the joint statement of the International Scientific Association for Probiotics and Prebiotics (ISAPP) on "Nature report" on the prebiotics in 2017, prebiotics are defined as "a substance that can be selectively utilized by microorganisms which are symbiotic with a host so as to promote the health of the host".

Probiotics in the digestive system (mainly the large intestines) can utilize prebiotics to grow, expand and metabolize in flora so as to generate short-chain fatty acids (SCFAs).

That is, the prebiotics can help the growth of probiotics and help to inhibit harmful bacteria in intestinal tracts. Probiotics in the intestinal tracts may also metabolize prebiotics to generate SCFAs, and then the SCFAs are provided for probiotics and the host as energy sources.

SUMMARY

In view of this, the present disclosure provides a prebiotic composition. The prebiotic composition includes a black tea ferment and a bioactive substance, can promote the growth ability of *Hafnia alvei* in the intestinal tract of a subject, and is used for helping the subject to lose weight.

In some embodiments, the prebiotic composition includes the black tea ferment and the bioactive substance. The bioactive substance is soybean peptide powder, pea protein, rice protein, corn oligopeptide powder, or a combination thereof. The black tea ferment is prepared by the following steps: extracting tea leaves of *Camellia sinensis* with water at 50° C. to 100° C. for 0.5 hours to 3 hours to obtain a black tea extract, and fermenting the black tea extract with *Saccharomyces cerevisiae* BCRC20271, *Bifidobacterium lactis* BCRC910887, *Lactobacillus gasseri* BCRC910886, and *Gluconacetobacter xylinus* BCRC12335 for 12 days to 25 days to obtain the black tea ferment.

In some embodiments, use of a prebiotic composition in preparation of a composition for weight loss is provided. The prebiotic composition includes a black tea ferment and a bioactive substance. The bioactive substance is soybean peptide powder, pea protein, rice protein, corn oligopeptide powder, or a combination thereof. The black tea ferment is prepared by the following steps: extracting tea leaves of *Camellia sinensis* with water at 50° C. to 100° C. for 0.5 hours to 3 hours to obtain the black tea extract, and fermenting the black tea extract with *Saccharomyces cerevisiae* BCRC20271, *Bifidobacterium lactis* BCRC910887, *Lactobacillus gasseri* BCRC910886, and *Gluconacetobacter xylinus* BCRC12335 for 12 days to 25 days to obtain the black tea ferment.

In some embodiments, a method for weight loss of a subject in need includes: administering an effective dose of a prebiotic composition to the subject in need. The prebiotic composition includes a black tea ferment and a bioactive substance. The bioactive substance is soybean peptide powder, pea protein, rice protein, corn oligopeptide powder, or a combination thereof. The black tea ferment is prepared by the following steps: extracting tea leaves of *Camellia sinensis* with water at 50° C. to 100° C. for 0.5 hours to 3 hours to obtain the black tea extract, and fermenting the black tea extract with *Saccharomyces cerevisiae* BCRC20271, *Bifidobacterium lactis* BCRC910887, *Lactobacillus gasseri* BCRC910886, and *Gluconacetobacter xylinus* BCRC12335 for 12 days to 25 days to obtain the black tea ferment.

In some embodiments, a weight ratio of the black tea ferment to the bioactive substance is 9:1 to 1:9.

In some embodiments, the prebiotic composition further includes erythritol, Arabic gum or a combination thereof.

In some embodiments, the prebiotic composition includes the black tea ferment, the bioactive substance and erythritol or Arabic gum; and a weight ratio of the black tea ferment to the bioactive substance to erythritol or Arabic gum is 1:1:0.05-2.

In some embodiments, the prebiotic composition includes the black tea ferment, the bioactive substance and erythritol; and a weight ratio of the black tea ferment to the bioactive substance to erythritol is 1:1:0.6-2.

In some embodiments, the prebiotic composition includes the black tea ferment, the bioactive substance and the Arabic gum; and a weight ratio of the black tea ferment to the bioactive substance to Arabic gum is 1:1:0.05-0.2.

In some embodiments, the prebiotic composition includes the black tea ferment, the bioactive substance, erythritol and Arabic gum; and a weight ratio of the black tea ferment to the bioactive substance to erythritol to Arabic gum is 1:1:0.6-2:0.05-0.2.

In some embodiments, the prebiotic composition includes the black tea ferment, the bioactive substance, erythritol and Arabic gum; and the weight ratio of the black tea ferment to the bioactive substance to erythritol to Arabic gum is 3:3:3.6:0.4.

In some embodiments, the bioactive substance is the soybean peptide powder.

In some embodiments, the prebiotic composition has an ability to promote the growth of *Hafnia alvei*.

In some embodiments, the prebiotic composition has an ability to increase the content of short-chain fatty acids (SCFAs) in intestinal tracts.

In some embodiments, the prebiotic composition has an ability to inhibit the appetite of the subject.

In some embodiments, the prebiotic composition has an ability to lose weight, and reduce body fat and waist circumference of the subject.

In some embodiments, the body fat is trunk body fat.

In some embodiments, the effective dose of the prebiotic composition is 500 g. In some embodiments, the prebiotic composition is administered twice a day.

In some embodiments, the composition for weight loss is in a capsule form and includes 500 g of the prebiotic composition.

In some embodiments, the composition for weight loss in the capsule form is administered twice a day.

In conclusion, the prebiotic composition according to any embodiment includes the black tea ferment and the bioactive substance, and has the abilities to promote *Hafnia alvei*, increase the content of the SCFAs in the intestinal tract, inhibit the appetite of the subject, lose the weight, and reduce the body fat (such as trunk body fat) and waist circumference of the subject. Moreover, the prebiotic composition can be used for preparing a composition for weight loss so as to help the subject to lose weight.

DETAILED DESCRIPTION

Figure 1:
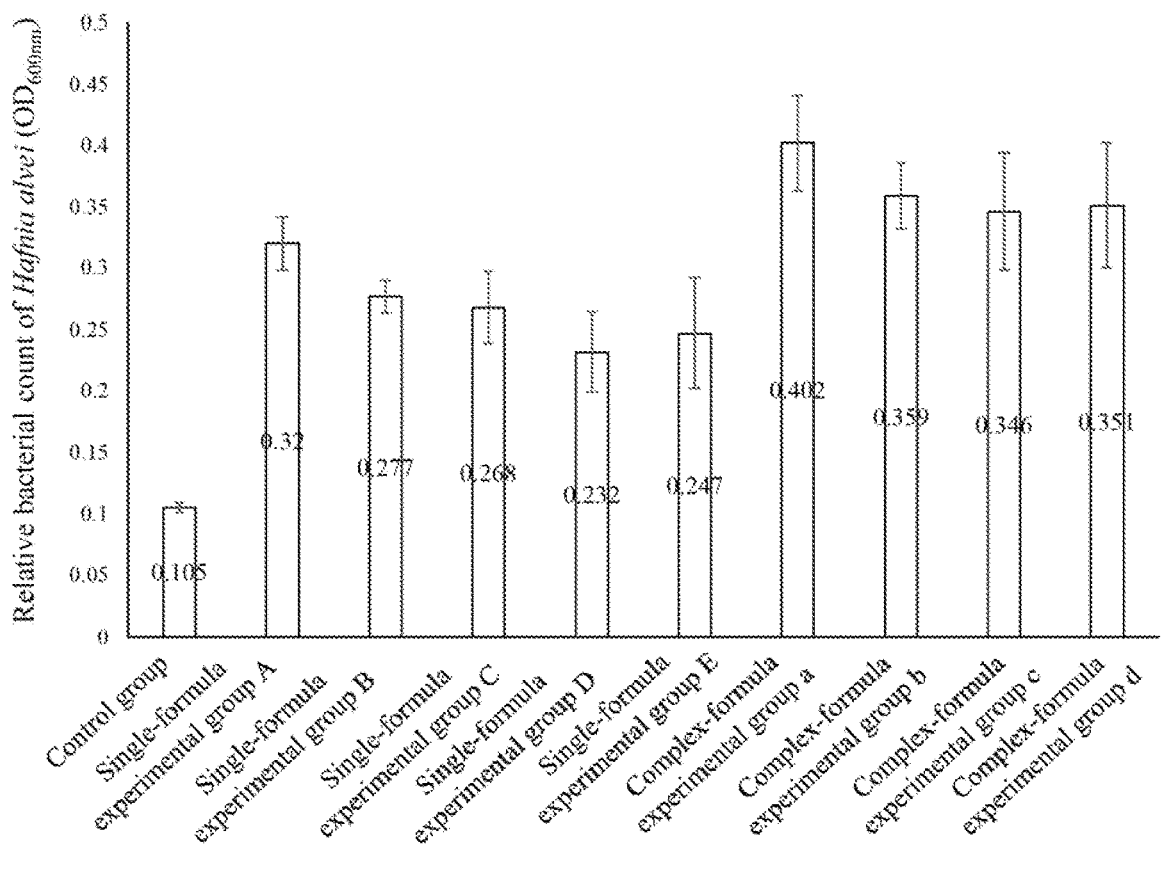
FIG. 1 is a diagram of an analysis experiment result of influence of a single ingredient and complex ingredients on *Hafnia alvei;*

In the description of the following embodiments, unless otherwise specified, the symbol "%" refers to weight percentage, and the symbol "vol %" usually refers to volume percentage concentration.

A prebiotic composition includes a black tea ferment and a bioactive substance. The bioactive substance is a nitrogen-containing amino acid composition, such as peptide, oligopeptide, and protein. For example, the bioactive substance is soybean peptide powder, pea protein, rice protein, corn oligopeptide powder or a combination thereof. The black tea ferment is prepared by extracting tea leaves of *Camellia sinensis* with water and then fermenting with a plurality of strains.

In some embodiments, the soybean peptide powder, the pea protein, the rice protein and the corn oligopeptide powder are commercially available. For example, the soybean peptide powder can be purchased from FUJI OIL Co. Ltd., the pea protein can be purchased from Roquette, France, the rice protein can be purchased from Panel Japan Co. Ltd., Japan, and the corn oligopeptide powder is purchased from ZHONGSHIDUQING (SHANDONG) Biological Co. Ltd., China.

In some embodiment, the bioactive substance is preferably the soybean peptide powder.

In some embodiments, the black tea ferment is prepared by the following steps: mixing tea leaves of *Camellia sinensis* with water, and extracting at 50° C. to 100° C. for 0.5 hours to 3 hours to obtain a black tea extract; and then, fermenting the black tea extract which is cooled to reach room temperature for 12 days to 25 days by *Saccharomyces cerevisiae* BCRC20271 (International deposit number: ATCC26602), *Bifidobacterium lactis* BCRC910887 (International deposit number: DSM33303), *Lactobacillus gasseri* BCRC910886 (International deposit number: DSM33105) and *Gluconacetobacter xylinus* BCRC12335 to obtain the black tea ferment.

In some embodiments, the weight ratio of the tea leaves of the black tea to the water is 1:(50-125). For example, the weight ratio of the tea leaves to the water is 1:100.

In some embodiments, the black tea extract is subjected to extraction at a temperature of 90° C. for 1.2 hours. Moreover, sterilization can be performed while extraction.

In some embodiments, the inoculum size of *Saccharomyces cerevisiae* BCRC20271 is 0.01%-0.5% (v/v), the inoculum size of *Bifidobacterium lactis* BCRC910887 is 0.01%-0.25% (v/v), the inoculum size of *Lactobacillus gasseri* BCRC910886 is 0.01%-0.25% (v/v), and the inoculum size of *Gluconacetobacter xylinus* BCRC12335 is 10%-15% (v/v). For example, the inoculum size of *Saccharomyces cerevisiae* BCRC20271 is 0.15% (v/v), the inoculum size of *Bifidobacterium lactis* BCRC910887 is 0.03% (v/v), the inoculum size of *Lactobacillus gasseri* BCRC910886 is 0.035% (v/v), and the inoculum size of *Gluconacetobacter xylinus* BCRC12335 is 12% (v/v).

In some embodiments, the *Saccharomyces cerevisiae* BCRC20271, the *Bifidobacterium lactis* BCRC910887, the *Lactobacillus gasseri* BCRC910886 and the *Gluconacetobacter xylinus* BCRC12335 are simultaneously implanted into the black tea extract, and are totally fermented for 14 days.

For example, the *Saccharomyces cerevisiae* BCRC20271, the *Bifidobacterium lactis* BCRC910887, the *Lactobacillus gasseri* BCRC910886 and the *Gluconacetobacter xylinus* BCRC12335 can be strains purchased from Food Industry Research and Development Institute. In addition, the international deposit number of the *Saccharomyces cerevisiae* BCRC20271 is ATCC26602, the international deposit number of the *Bifidobacterium lactis* BCRC910887 is DSM33303, the international deposit number of the *Lactobacillus gasseri* BCRC910886 is DSM33105, and the *Gluconacetobacter xylinus* BCRC12335 can be seen in a Taiwan Application with the application number as TW201819635A.

In some embodiments, steps for preparing the black tea ferment further includes: performing vacuum concentration at 45° C. to 70° C. after fermenting the black tea extract for 12 days to 25 days; adjusting Brix of the obtained product to 4.1±0.5°Bx (this is a condition for quality control and management); and then filtering by a sieve with 200-400 meshes to obtain the black tea ferment.

In some examples, the tea leaves of *Camellia sinensis* are mixed with water according to a weight ratio of 1:50-125, and extraction is carried out for 0.5 hours to 3 hours at the temperature of 50° C. to 100° C. to obtain the black tea extract. After the black tea extract is cooled to reach room temperature, 0.01%-0.5% (v/v) of *Saccharomyces cerevisiae* BCRC20271, 0.01%-0.25% (v/v) of *Bifidobacterium lactis* BCRC910887, 0.01%-0.25% (v/v) of *Lactobacillus gasseri* BCRC910886 and 10%-15% (v/v) of Gluconacetobacter xylinus BCRC12335 are synchronously inoculated to the cooled black tea extract and fermented. A primary black tea ferment solution is obtained after 12 days to 25 days. The primary black tea fermentation solution is subjected to vacuum concentration at 45° C. to 70° C., and the Brix is adjusted to be 4.1±0.5° Bx; and then filtering is carried out by the sieve with 200-400 meshes to obtain the black tea ferment.

In some embodiments, the prebiotic composition includes the black tea ferment and the bioactive substance in a weight ratio of 9:1 to 1:9. In some other preferred embodiments, the weight ratio of the black tea ferment to the bioactive substance is 4-7:6-3. In still some other preferred embodiments, the weight ratio of the black tea ferment to the bioactive substance is 1:1.

In some embodiments, the prebiotic composition further includes carbohydrate compounds and derivatives thereof. For example, the carbohydrate compounds and derivatives thereof include erythritol, arabinose, Arabic gum, fructooligosaccharide and the like. In some embodiments, the prebiotic composition further includes erythritol, Arabic gum or a combination thereof For example, the prebiotic composition is a combination of the black tea ferment and the bioactive substance, a combination of the black tea ferment, the bioactive substance and erythritol, a combination of the black tea ferment, the bioactive substance and Arabic gum, and a combination of the black tea ferment, the bioactive substance, erythritol and Arabic gum.

In some embodiments, the prebiotic composition includes the black tea ferment, the bioactive substance and erythritol in a weight ratio of 1:1:1. In some other embodiments, the weight ratio of the black tea ferment to the bioactive substance to erythritol is 1:1:0.6-2.

In some embodiments, the prebiotic composition includes the black tea ferment, the bioactive substance and Arabic gum in a weight ratio of 1:1:1. In some other embodiments, the weight ratio of the black tea ferment to the bioactive substance to Arabic gum is 1:1:(0.05-0.2).

In some embodiments, the prebiotic composition includes the black tea ferment, the bioactive substance, erythritol and Arabic gum in a weight ratio 1:1:0.6-2:0.05-0.2. In some other embodiments, the weight ratio of the black tea ferment to the bioactive substance to erythritol to Arabic gum is 1:1:1.2:0.1. In still some other embodiments, the weight ratio of the black tea ferment to the bioactive substance to erythritol to Arabic gum is 3:3:3.6:0.4.

Therefore, the black tea ferment obtained by a specific process can be mixed with the bioactive substance or the bioactive substance and the carbohydrate compounds in a specific proportion to obtain the prebiotic composition. The prebiotic composition can increase the quantity of specific probiotics in the intestinal tract of the subject by at least 7 folds.

In some embodiments, the prebiotic composition can improve the microflora of the intestinal tract. For example, the prebiotic composition can promote the growth of *Hafnia*

*alvei* in the intestinal tract of the subject so as to increase caseinolytic peptidase B (ClpB protein) and short-chain fatty acids (SCFAs).

In some embodiments, the prebiotic composition can inhibit the appetite of the subject. For example, by taking the prebiotic composition, the satiety of the subject is increased, and the appetite can be inhibited, and thus excessive or excessive intake is reduced.

In some embodiments, the prebiotic composition can lose the weight, and reduce the body fat and waist circumference of the subject. For example, the body fat is trunk body fat.

Therefore, the prebiotic composition can be used for preparing a composition for weight loss.

In some embodiments, the composition for weight loss can be in a solid form, such as powder, a tablet and a capsule. For example, the composition for weight loss is in a capsule form, and contains 500 g of the prebiotic composition.

In some embodiments, the dosage of the prebiotic composition is 1,000 mg/d. For example, the prebiotic composition mainly includes the black tea ferment, the soybean peptide powder, erythritol and Arabic gum. 1,000 mg of the prebiotic composition per day means that the total amount of the black tea ferment, the soybean peptide powder, erythritol and Arabic gum is 1,000 mg.

In some embodiments, the composition for weight loss in the capsule form contains 500 g of the prebiotic composition, and is administrated twice per day.

Any one of the abovementioned prebiotic compositions can be a medicine. In other words, the medicine contains an effective content of the combination of the black tea ferment and the bioactive substance (such as the soybean peptide powder) in a specific proportion, or the combination of the black tea ferment, the bioactive substance (such as the soybean peptide powder), erythritol and/or Arabic gum.

In some embodiments, the aforementioned medicine can be made into dosage forms suitable for enteral, parenteral, oral, or topical administration using technologies well-known to those skilled in the art.

In some embodiments, the dosage forms suitable for enteral or oral administration can be, but are not limited to, the form of a tablet, a troche, a lozenge, a pill, a capsule, dispersible powder or granule, a solution, a suspension, an emulsion, syrup, an elixir, slurry or the like. In some embodiments, the dosage forms suitable for parenteral or topical administration can be, but are not limited to, the form of an injection, sterile powder, external preparation or the like. In some embodiments, the injection can be administrated by subcutaneous injection, intraepidermal injection, intradermal injection or intralesional injection.

In some embodiments, the medicine may include a pharmaceutically acceptable carrier which is widely applied to medicine manufacturing technologies. In some embodiments, the pharmaceutically acceptable carrier can be one or more of the following carriers: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome and the like. The types and quantity of the carriers to be the adopted are within the expertise and routine skill of those skilled in the art. In some embodiments, the pharmaceutically acceptable carrier may be water, normal saline, phosphate buffered saline (PBS), and aqueous solution containing alcohol.

In some embodiments, any of the abovementioned prebiotic compositions can be an edible product. In other words, the edible product includes a specific content of the combination of the black tea ferment and the bioactive substance (such as the soybean peptide powder) in a specific proportion, or the combination of the black tea ferment, the bioactive substance (such as the soybean peptide powder), erythritol and/or Arabic gum. In some embodiments, the edible product can be a general food, a healthcare food or a dietary supplement.

In some embodiments, the abovementioned edible product can be made into a dosage form suitable for oral administration using technologies well-known to those skilled in the art. In some embodiments, the abovementioned general food can be the edible product. In some embodiments, the general food can be, but is not limited to, beverages, fermented foods, baked products, or seasonings.

In some embodiments, the obtained prebiotic composition can be further used as a food additive to prepare a food composition containing the prebiotic composition prepared from the combination of the black tea ferment and the bioactive substance (such as the soybean peptide powder) in a specific proportion, or the combination of the black tea ferment, the bioactive substance (such as the soybean peptide powder), erythritol and/or Arabic gum in a specific proportion. Therefore, the prebiotic composition according to any embodiment can be added during raw material preparation by a known method, or the prebiotic composition according to any embodiment can be added in the food making process so as to be matched with any edible materials to prepare the edible product (namely the food composition) for human and non-human animals to eat.

Embodiment 1: Preparation of Black Tea Ferment

Tea leaves of *Camellia sinensis* (purchased from TAI-WAN TEA CORPORATION) was mixed with water according to a weight ratio of 1:100, and the obtained mixture was extracted at 90° C. for 1.2 hours to obtain a black tea extract. After the black tea extract was cooled to reach room temperature, 0.015% (v/v) of *Saccharomyces cerevisiae* BCRC20271, 0.03% (v/v) of *Bifidobacterium lactis* BCRC910887, 0.035% (v/v) of *Lactobacillus gasseri* BCRC910886 and 12% (v/v) of *Gluconacetobacter xylinus* BCRC12335 were synchronously inoculated to the cooled black tea extract, and fermented for 14 days to obtain a primary black tea fermentation solution. The primary black tea fermentation solution was subjected to vacuum concentration at 45° C. to 70° C., and the Brix was adjusted to be 4.1±0.5°Bx. Then filtering was carried out by a sieve with 200-400 meshes to obtain the black tea ferment.

The *Saccharomyces cerevisiae* BCRC20271, the *Bifidobacterium lactis* BCRC910887, the *Lactobacillus gasseri* BCRC910886 and the *Gluconacetobacter xylinus* BCRC12335 were strains purchased from Food Industry Research and Development Institute (FIRDI).

Embodiment 2: Influence of Single Ingredient and Complex Ingredients on *Hafnia alvei*

The single ingredient referred to 5 prebiotics (hereinafter referred to as a single-ingredient formula), including the black tea ferment prepared in Embodiment 1, soybean peptide powder (purchased from FUJI OIL Co. Ltd.), pea protein (purchased from Roquette, France), rice protein (purchased from Panel Japan Co. Ltd., Japan), and corn oligopeptide powder (purchased from ZHONG-SHIDUQING (SHANDONG) Biological Co. Ltd., China), and there were five single-formula experimental groups from a single-formula experimental group A to a single-formula experimental group E. The complex ingredients referred to prebiotic compositions (hereinafter referred to as a complex-ingredient formula) formed by combinations of the black tea ferment prepared in Embodiment 1 and 4 bioactive substances (namely soybean peptide powder, pea protein, rice protein and corn oligopeptide powder), and there were 4 complex-formula experimental groups from a complex-formula experimental group a to a complex-formula experimental group d. An adopted liquid medium was a brain heart infusion broth (BHI, hereinafter referred to as a BHI medium, and purchased from Difco™). Adopted test strains were *Hafnia alvei* BCRC10906 purchased from Bioresource Collection and Research Center (BCRC).

The groups were divided into a control group, five single-formula experimental groups and four complex-formula experimental groups, as shown in Table 1.

Control group: No formula was added, and an experimental medium was 10 ml of the BHI medium.

Single-formula experimental group: A single-formula experimental group A containing the black tea ferment prepared in Embodiment 1, a single-formula experimental group B containing the soybean peptide powder, a single-formula experimental group C containing the pea protein, a single-formula experimental group D containing the rice protein and a single-formula experimental group E containing the corn oligopeptide powder. Moreover, the experimental medium of the single-formula experimental group A was 10 ml of the BHI medium containing 1 g of the black tea ferment prepared in Embodiment 1. The experimental medium of the single-formula experimental group B was 10 ml of the BHI medium containing 1 g of the soybean peptide powder. The experimental medium of the single-formula experimental group C was 10 ml of the BHI medium containing 1 g of the pea protein. The experimental medium of the single-formula experimental group D was 10 ml of the BHI medium containing 1 g of the rice protein. The experimental medium of the single-formula experimental group E was 10 ml of the BHI medium containing 1 g of the corn oligopeptide powder.

Complex-formula experimental group: A complex-formula experimental group a containing the black tea ferment prepared in Embodiment 1 and the soybean peptide powder, a complex-formula experimental group b containing the black tea ferment prepared in Embodiment 1 and the pea protein, a complex-formula experimental group c containing the black tea ferment prepared in Embodiment 1 and the rice protein, and a complex-formula experimental group d containing the black tea ferment prepared in Embodiment 1 and the corn oligopeptide powder. The experimental medium of the complex-formula experimental group a was 10 ml of the BHI medium containing 0.5 g of the black tea ferment prepared in Embodiment 1 and 0.5 g of the soybean peptide powder. The experimental medium of the complex-formula experimental group b was 10 ml of the BHI medium containing 0.5 g of the black tea ferment prepared in Embodiment 1 and 0.5 g of the pea protein. The experimental medium of the complex-formula experimental group c was 10 ml of the BHI medium containing 0.5 g of the black tea ferment prepared in Embodiment 1 and 0.5 g of the rice protein. The experimental medium of the complex-formula experimental group d was 10 ml of the BHI medium containing 0.5 g of the black tea ferment prepared in Embodiment 1 and 0.5 g of the corn oligopeptide powder.

TABLE 1

| Group | Formula (single ingredient and complex ingredients) | Experimental medium (10 mL) |
|---|---|---|
| Control group | — | BHI medium |
| Single-formula experimental group A | Single-ingredient formula A: Black tea ferment prepared in Embodiment 1 | 10 mL of BHI medium containing 1 g of single-ingredient formula A |
| Single-formula experimental group B | Single-ingredient formula B: Soybean peptide powder | 10 mL of BHI medium containing 1 g of single-ingredient formula B |
| Single-formula experimental group C | Single-ingredient formula C: Pea protein | 10 mL of BHI medium containing 1 g of single-ingredient formula C |
| Single-formula experimental group D | Single-ingredient formula D: Rice protein | 10 mL of BHI medium containing 1 g of single-ingredient formula D |
| Single-formula experimental group E | Single-ingredient formula E: Corn oligopeptide powder | 10 mL of BHI medium containing 1 g of single-ingredient formula E |
| Complex-formula experimental group a | Complex-ingredient formula a: Black tea ferment prepared in Embodiment 1 and soybean peptide powder (weight ratio of 1:1) | 10 mL of BHI medium containing 1 g of complex-ingredient formula a |
| Complex-formula experimental group b | Complex-ingredient formula b: Black tea ferment prepared in Embodiment 1 and pea protein (weight ratio of 1:1) | 10 mL of BHI medium containing 1 g of complex-ingredient formula b |
| Complex-formula experimental group c | Complex-ingredient formula c: Black tea ferment prepared in Embodiment 1 and rice protein (weight ratio of 1:1) | 10 mL of BHI medium containing 1 g of complex-ingredient formula c |
| Complex-formula experimental group d | Complex-ingredient formula d: Black tea ferment prepared in Embodiment 1 and corn oligopeptide powder (weight ratio of 1:1) | 10 mL of BHI medium containing 1 g of complex-ingredient formula d |

Firstly, 5% (v/v) of *Hafnia alvei* was inoculated to the BHI medium, and activated in an anaerobic operation box (5% of hydrogen, 10% of carbon dioxide and 85% of nitrogen) at 37° C. for 24 hours to obtain an experimental bacterial solution.

5% (v/v) of activated *Hafnia alvei* was added into each of test tubes filled with 10 mL of the experimental medium of each group respectively, and subjected to anaerobic culture at 37° C. for 24 hours; and double repeated experiments were carried out. Then, after culturing for 24 hours, the bacterial solution of each group was shaken up. 200 µl of the bacterial solution was charged into to a 96-well plate. $OD_{600nm}$ of each group was detected within 15 minutes through a disc-type full-spectrum optical quantometer (Brand: BioTek; Model: EPOCH). The absorbance of the control group was regarded as the relative bacterial count of 100±3.81%, and the relative bacterial count (%) of other groups was correspondingly converted. The detection result and the converted relative bacterial count result are shown in FIG. 1 and Table 2.

TABLE 2

| Group | Absorbance ($OD_{600}$) | Relative bacterial count (%) |
|---|---|---|
| Control group | 0.105 ± 0.004 | 100 ± 3.81 |
| Single-formula experimental group A | 0.32 ± 0.022 | 304.77 ± 20.96 |
| Single-formula experimental group B | 0.277 ± 0.013 | 263.81 ± 12.39 |
| Single-formula experimental group C | 0.268 ± 0.029 | 255.24 ± 27.62 |
| Single-formula experimental group D | 0.232 ± 0.033 | 220.96 ± 22.63 |

TABLE 2-continued

| Group | Absorbance ($OD_{600}$) | Relative bacterial count (%) |
|---|---|---|
| Single-formula experimental group E | 0.247 ± 0.045 | 235.24 ± 39.26 |
| Complex-formula experimental group a | 0.402 ± 0.039 | 382.86 ± 37.15 |
| Complex-formula experimental group b | 0.359 ± 0.027 | 341.91 ± 25.72 |
| Complex-formula experimental group c | 0.346 ± 0.041 | 361.91 ± 39.05 |
| Complex-formula experimental group d | 0.351 ± 0.051 | 342.86 ± 35.66 |

As shown in FIG. 1, the $OD_{600nm}$ of the control group without any prebiotics was 0.105±0.004. In the 9 experimental groups, the $OD_{600nm}$ of the single-formula experimental group A was 0.32±0.022, the $OD_{600nm}$ of the single-formula experimental group B was 0.227±0.013, the $OD_{600nm}$ of the single-formula experimental group C was 0.268±0.029, the $OD_{600nm}$ of the single-formula experimental group D was 0.232±0.033, the $OD_{600nm}$ of the single-formula experimental group E was 0.247±0.045, the $OD_{600nm}$ of the complex-formula experimental group a was 0.402±0.039, the $OD_{600nm}$ of the complex-formula experimental group b was 0.359±0.027, the $OD_{600nm}$ of the complex-formula experimental group c was 0.356±0.041, and the $OD_{600nm}$ of the complex-formula experimental group d was 0.351±0.051. Therefore, the complex-ingredient formula had the *Hafnia alvei* growth promoting effect better than that of the single-ingredient formula. The complex-ingredient formula a (the black tea ferment prepared in Embodiment 1 and the soybean peptide powder in the weight ratio of 1:1) had the most significant ability to promote the growth of *Hafnia alvei*, and the relative bacterial count of the complex-formula experimental group a was about 4 folds that of the control group.

Embodiment 3: Influence of Multiple Groups of Prebiotic Compositions (a Black Tea Ferment and Soybean Peptide Powder) in Different Proportions on *Hafnia alvei*

The groups were divided into a control group and 9 experimental groups. The adopted liquid medium was a brain heart infusion broth (BHI, hereinafter referred to as a BHI medium, and purchased from Difco™). The adopted test strains were *Hafnia alvei* BCRC10906 purchased from Bioresource Collection and Research Center (BCRC). Each group is shown as Table 3.

Control group: No prebiotics were added, and the experimental medium was 10 ml of the BHI medium.

9 Experimental groups: Experimental group [1] to experimental group [9] containing the black tea ferment prepared in Embodiment 1 and the soybean peptide powder in different proportions. The weight ratio of the prebiotic composition in the experimental groups was 1:9 to 9:1. The experimental medium of each group was 10 ml of the BHI medium containing 1 g of the prebiotic composition (namely, a combination of 0.1 g of the black tea ferment prepared in Embodiment 1 and 0.9 g of the soybean peptide powder, a combination of 0.2 g of the black tea ferment prepared in Embodiment 1 and about 0.8 g of the soybean peptide powder, a combination of 0.3 g of the black tea ferment prepared in Embodiment 1 and 0.7 g of the soybean peptide powder, a combination of 0.4 g of the black tea ferment prepared in Embodiment 1 and 0.6 g of the soybean peptide powder, a combination of 0.5 g of the black tea ferment prepared in Embodiment 1 and 0.5 g of the soybean peptide powder, a combination of 0.6 g of the black tea ferment prepared in Embodiment 1 and 0.4 g of the soybean peptide powder, a combination of 0.7 g of the black tea ferment prepared in Embodiment 1 and 0.3 g of the soybean peptide powder, a combination of 0.8 g of the black tea ferment prepared in Embodiment 1 and 0.2 g of the soybean peptide powder, and a combination of 0.9 g of the black tea ferment prepared in Embodiment 1 and 0.1 g of the soybean peptide powder). The 9 experimental groups are also referred to as formulas [1] to [9].

TABLE 3

| Group | Formula | Experimental medium (10 mL) |
|---|---|---|
| Control group | — | 10 mL BHI medium |
| Experimental group [1] | Formula [1]: Black tea ferment prepared in Embodiment 1 and soybean peptide powder in weight ratio of 1:9 | 10 mL of BHI medium containing 1 g of formula [1] |
| Experimental group [2] | Formula [2]: Black tea ferment prepared in Embodiment 1 and soybean peptide powder in weight ratio of 2:8 | 10 mL of BHI medium containing 1 g of formula [2] |
| Experimental group [3] | Formula [3]: Black tea ferment prepared in Embodiment 1 and soybean peptide powder in weight ratio of 3:7 | 10 mL of BHI medium containing 1 g of formula [3] |
| Experimental group [4] | Formula [4]: Black tea ferment prepared in Embodiment 1 and soybean peptide powder in weight ratio of 4:6 | 10 mL of BHI medium containing 1 g of formula [4] |
| Experimental group [5] | Formula [5]: Black tea ferment prepared in Embodiment 1 and soybean peptide powder in weight ratio of 5:5 | 10 mL of BHI medium containing formula [5] |
| Experimental group [6] | Formula [6]: Black tea ferment prepared in Embodiment 1 and soybean peptide powder in weight ratio of 6:4 | 10 mL of BHI medium containing formula [6] |
| Experimental group [7] | Formula [7]: Black tea ferment prepared in Embodiment 1 and soybean peptide powder in weight ratio of 7:3 | 10 mL of BHI medium containing 1 g of formula [7] |
| Experimental group [8] | Formula [8]: Black tea ferment prepared in Embodiment 1 and soybean peptide powder in weight ratio of 8:2 | 10 mL of BHI medium containing 1 g of formula [8] |
| Experimental group [9] | Formula [9]: Black tea ferment prepared in Embodiment 1 and soybean peptide powder in weight ratio of 9:1 | 10 mL of BHI medium containing 1 g of formula [9] |

Firstly, 5% (v/v) of *Hafnia alvei* was inoculated to the BHI medium, and activated in an anaerobic operation box (5% of hydrogen, 10% of carbon dioxide and 85% of nitrogen) at 37° C. for 24 hours to obtain an experimental bacterial solution.

5% (v/v) of activated *Hafnia alvei* was added into each of test tubes filled with 10 mL of the experimental medium of each group respectively, and subjected to anaerobic culture at 37° C. for 24 hours; and double repeated experiments were carried out. Then, after culturing for 24 hours, the bacterial solution of each group was shaken up. 200 μl of the bacterial solution was charged into to a 96-well plate. $OD_{600nm}$ of each group was detected within 15 minutes through a disc-type full-spectrum optical quantometer (Brand: BioTek; Model: EPOCH). The absorbance of the control group was regarded as the relative bacterial count of 100±11.2%, and the relative bacterial count (%) of other groups was correspondingly converted. The detection result and the converted relative bacterial count result are shown in FIG. 2 and Table 4.

TABLE 4

| Group | Absorbance ($OD_{600}$) | Relative bacterial count (%) |
|---|---|---|
| Control group | 0.098 ± 0.011 | 100 ± 11.2 |
| Experimental group [1] | 0.303 ± 0.019 | 309 ± 19.4 |
| Experimental group [2] | 0.279 ± 0.032 | 285 ± 32.7 |
| Experimental group [3] | 0.290 ± 0.028 | 296 ± 28.6 |
| Experimental group [4] | 0.362 ± 0.023 | 369 ± 23.5 |
| Experimental group [5] | 0.489 ± 0.056 | 499 ± 11.45 |
| Experimental group [6] | 0.377 ± 0.065 | 385 ± 66.3 |
| Experimental group [7] | 0.317 ± 0.041 | 323 ± 41.8 |
| Experimental group [8] | 0.302 ± 0.035 | 308 ± 35.7 |
| Experimental group [9] | 0.265 ± 0.047 | 270 ± 48.0 |

Figure 2:
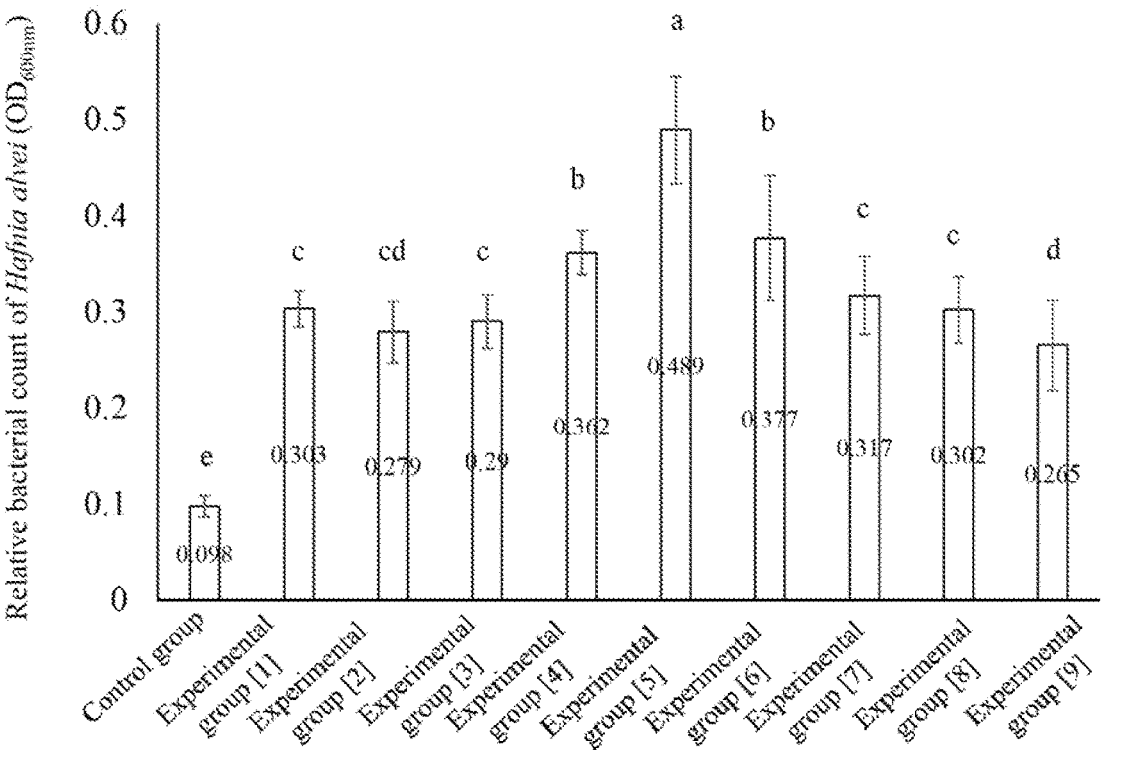
FIG. 2 is a diagram of an analysis experiment result of influence of multiple groups of prebiotic compositions (a black tea ferment and soybean peptide powder) in different proportions on *Hafnia alvei;*

As shown in FIG. 2, the $OD_{600nm}$ of the control group without any prebiotics was 0.098±0.011e. In the rest 9 experimental groups, the $OD_{600nm}$ of the experimental group [1] was 0.303±0.019c, the $OD_{600nm}$ of the experimental group [2] was 0.279±0.032cd, the $OD_{600nm}$ of the experimental group [3] was 0.290±0.028c, the $OD_{600nm}$ of the experimental group [4] was 0.362±0.023b, the $OD_{600nm}$ of the experimental group [5] was 0.489±0.056a, the $OD_{600nm}$ of the experimental group [6] was 0.377±0.065b, the $OD_{600nm}$ of the experimental group [7] was 0.317±0.041c, the $OD_{600nm}$ of the experimental group [8] was 0.302±0.035c, and the $OD_{600nm}$ of the experimental group [9] was 0.265±0.047d. Therefore, both the black tea ferment prepared in Embodiment 1 and the soybean peptide powder in 9 composing proportions promoted the growth of *Hafnia alvei*, but when the weight ratio of the black tea ferment prepared in Embodiment 1 to the soybean peptide powder is 1:1, the growth promotion ability was relatively remarkable, and the relative bacterial count was about 5 folds that of the control group.

Embodiment 4: Influence of Multiple Groups of
Prebiotic Compositions in Different Combinations
on *Hafnia alvei*

The groups were divided into a control group and 11 experimental groups. The experimental groups included 6 single-formula experimental groups and 5 complex-formula experimental groups, namely a single-formula experimental group [1] to a single-formula experimental group [6], and a complex-formula experimental group [1] to a complex-formula experimental group [5]. The adopted liquid medium was a brain heart infusion broth (BHI, hereinafter referred to as the BHI medium, and purchased from Difco™). The adopted test strains were *Hafnia alvei* BCRC10906 purchased from Bioresource Collection and Research Center (BCRC). Each group is shown as Table 5.

Control group: No prebiotics were added, and the experimental medium was 10 ml of the BHI medium.

6 single-formula experimental groups: A single-formula experimental group [1] containing erythritol (purchased from SWEET TOWN ENTERPRISE CORP.), a single-formula experimental group [2] containing arabinose (purchased from HIGHCHEM Co., Ltd.), a single-formula experimental group [3] containing Arabic gum (purchased from Buildmore Enterprise Co., Ltd.), a single-formula experimental group [4] containing fructooligosaccharide (purchased from Panel Japan Co., Ltd.), a single-formula experimental group [5] containing soybean peptide powder (purchased from FUJI OIL Co. Ltd.), and a single-formula experimental group [6] containing the black tea ferment prepared in Embodiment 1. The experimental medium of each group was 10 ml of the BHI medium containing 1 g of prebiotics (namely, erythritol, arabinose, Arabic gum, fructooligosaccharide, soybean peptide powder, the black tea ferment prepared in Embodiment 1. The 6 single-formula experimental groups were also called single-ingredient formulas [1] to [6]).

5 complex-formula experimental groups: A complex-formula experimental group [1] containing the black tea ferment prepared in Embodiment 1 and the soybean peptide powder; a complex-formula experimental group [2] containing the black tea ferment prepared in Embodiment 1, the soybean peptide powder and erythritol; a complex-formula experimental group [3] containing the black tea ferment prepared in Embodiment 1, the soybean peptide powder and fructooligosaccharide ; a complex-formula experimental group [4] containing the black tea ferment prepared in Embodiment 1, the soybean peptide powder and arabinose; and a complex-formula experimental group [5] containing the black tea ferment prepared in Embodiment 1, the soybean peptide powder and Arabic gum. The weight ratio of the prebiotic compositions of the complex-formula experimental groups was 1:1 or 1:1:1. The experimental medium of each group was 10 ml of the BHI medium containing 1 g of prebiotic composition (namely, a combination of 0.5 g of the black tea ferment prepared in Embodiment 1 and 0.5 g of the soybean peptide powder, a combination of about 0.33 g of the black tea ferment prepared in Embodiment 1, about 0.33 g of the soybean peptide powder and about 0.33 g of erythritol, a combination of about 0.33 g of the black tea ferment prepared in Embodiment 1, about 0.33 g of the soybean peptide powder and about 0.33 g of fructooligosaccharide , a combination of about 0.33 g of the black tea ferment prepared in Embodiment 1, about 0.33 g of the soybean peptide powder and about 0.33 g of arabinose, and a combination of about 0.33 g of the black tea ferment prepared in Embodiment 1, about 0.33 g of the soybean peptide powder and about 0.33 g of Arabic gum; and the 5 complex-formula experimental groups are also referred to as complex-ingredient formulas [1] to [5]).

TABLE 5

| Group | Formula (single ingredient and complex ingredients) | Experimental medium (10 mL) |
|---|---|---|
| Control group | — | BHI medium |
| Single-formula experimental group [1] | Single-ingredient formula [1]: Erythritol | 10 mL of BHI medium containing 1 g of single-ingredient formula [1] |
| Single-formula experimental group [2] | Single-ingredient formula [2]: Arabinose | 10 mL of BHI medium containing 1 g of single-ingredient formula [2] |
| Single-formula experimental group [3] | Single-ingredient formula [3]: Arabic gum | 10 mL of BHI medium containing 1 g of single-ingredient formula [3] |
| Single-formula experimental group [4] | Single-ingredient formula [4]: Fructooligosaccharide | 10 mL of BHI medium containing 1 g of single-ingredient formula [4] |
| Single-formula experimental group [5] | Single-ingredient formula [5]: Soybean peptide powder | 10 mL of BHI medium containing single-ingredient formula [5] |
| Single-formula experimental group [6] | Single-ingredient formula [6]: Black tea ferment prepared in Embodiment 1 | 10 mL of BHI medium containing single-ingredient formula [6] |
| Complex-formula experimental group [1] | Complex-ingredient formula [1]: Black tea ferment prepared in Embodiment 1 and soybean peptide powder (weight ratio of 1:1) | 10 mL of BHI medium containing 1 g of complex-ingredient formula [1] |
| Complex-formula experimental group [2] | Complex-ingredient formula [2]: Black tea ferment prepared in Embodiment 1, soybean peptide powder and erythritol (weight ratio of 1:1:1) | 10 mL of BHI medium containing 1 g of complex-ingredient formula [2] |
| Complex-formula experimental group [3] | Complex-ingredient formula [3]: Black tea ferment prepared in Embodiment 1, soybean peptide powder and fructooligosaccharide (weight ratio of 1:1:1) | 10 mL of BHI medium containing 1 g of complex-ingredient formula [3] |
| Complex-formula experimental group [4] | Complex-ingredient formula [4]: Black tea ferment prepared in Embodiment 1, soybean peptide powder and arabinose (weight ratio of 1:1:1) | 10 mL of BHI medium containing 1 g of complex-ingredient formula [4] |
| Complex-formula experimental group [5] | Complex-ingredient formula [5]: Black tea ferment prepared in Embodiment 1, soybean peptide powder and Arabic gum (weight ratio of 1:1:1) | 10 mL of BHI medium containing 1 g of complex-ingredient formula [5] |

Firstly, 5% (v/v) of *Hafnia alvei* was inoculated to the BHI medium, and activated in an anaerobic operation box (5% of hydrogen, 10% of carbon dioxide and 85% of nitrogen) at 37° C. for 24 hours to obtain an experimental bacterial solution.

Figures 3, 4:
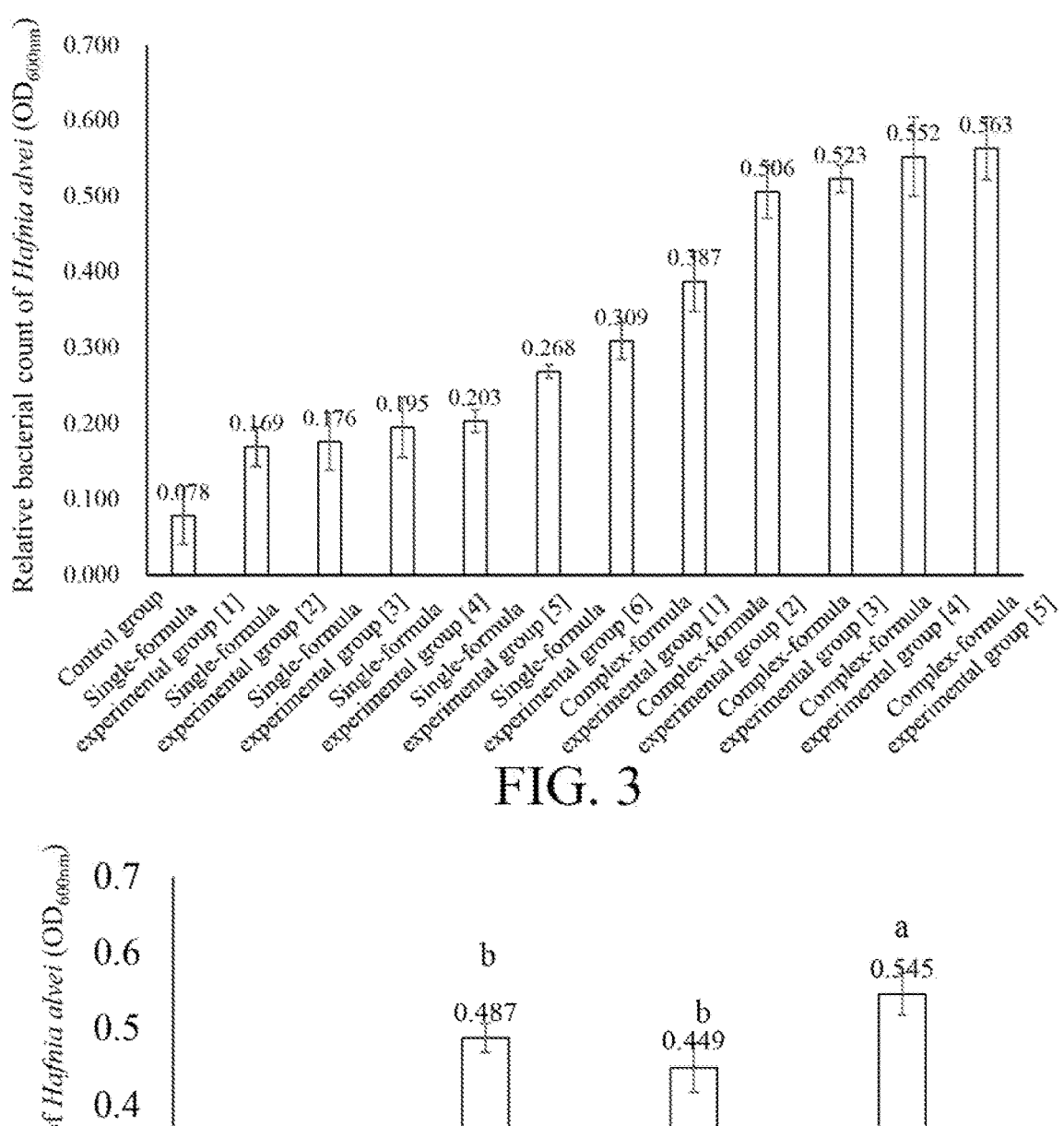
FIG. 3 is a diagram of an analysis experiment result of influence of multiple groups of prebiotic compositions in different combinations on *Hafnia alvei;*
FIG. 4 is a diagram of an analysis experiment result of influence of specific prebiotic compositions in different proportions on *Hafnia alvei;*

5% (v/v) of activated *Hafnia alvei* was added into each of test tubes filled with 10 mL of the experimental medium of each group respectively, and subjected to anaerobic culture at 37° C. for 24 hours; and double repeated experiments were carried out. Then, after culturing for 24 hours, the bacterial solution of each group was shaken up. 200 μl of the bacterial solution was charged into to a 96-well plate. $OD_{600nm}$ of each group was detected within 15 minutes through a disc-type full-spectrum optical quantometer (Brand: BioTek; Model: EPOCH). The absorbance of the control group was regarded as the relative bacterial count of 100±3.81%, and the relative bacterial count (%) of other groups was correspondingly converted. The detection result and the converted relative bacterial count result are shown in FIG. 3 and Table 6.

TABLE 6

| Group | Absorbance ($OD_{600}$) | Relative bacterial count (%) |
|---|---|---|
| Control group | 0.078 ± 0.039 | 100 ± 50 |
| Single-formula experimental group [1] | 0.169 ± 0.026 | 217 ± 34 |

TABLE 6-continued

| Group | Absorbance ($OD_{600}$) | Relative bacterial count (%) |
|---|---|---|
| Single-formula experimental group [2] | 0.176 ± 0.038 | 226 ± 49 |
| Single-formula experimental group [3] | 0.195 ± 0.04 | 250 ± 52 |
| Single-formula experimental group [4] | 0.203 ± 0.015 | 261 ± 20 |
| Single-formula experimental group [5] | 0.268 ± 0.009 | 344 ± 12 |
| Single-formula experimental group [6] | 0.309 ± 0.025 | 397 ± 33 |
| Complex-formula experimental group [1] | 0.387 ± 0.039 | 497 ± 50 |
| Complex-formula experimental group [2] | 0.506 ± 0.035 | 649 ± 45 |
| Complex-formula experimental group [3] | 0.523± 0.018 | 671 ± 24 |
| Complex-formula experimental group [4] | 0.552 ± 0.052 | 708 ± 67 |
| Complex-formula experimental group [5] | 0.563 ± 0.041 | 722 ± 53 |

As shown in FIG. 3, the $OD_{600nm}$ of the control group without any prebiotics was 0.078±0.039. In the 11 experimental groups, the $OD_{600nm}$ of the single-formula experimental group [1] was 0.169±0.026, the $OD_{600nm}$ of the single-formula experimental group [2] was 0.176±0.038, the $OD_{600nm}$ of the single-formula experimental group [3] was 0.195±0.04, the $OD_{600nm}$ of the single-formula experimental group [4] was 0.203±0.015, the $OD_{600nm}$ of the single-formula experimental group [5] was 0.268±0.009, the $OD_{600nm}$ of the single-formula experimental group [6] was 0.309±0.025, the $OD_{600nm}$ of the complex-formula experimental group [1] was 0.387±0.039, the $OD_{600nm}$ of the complex-formula experimental group [2] was 0.506±0.035, the $OD_{600nm}$ of the complex-formula experimental group [3] was 0.523±0.018, the $OD_{600nm}$ of the complex-formula experimental group [4] was 0.552±0.052, and the $OD_{600nm}$ of the complex-formula experimental group [5] was 0.563±0.041. Therefore, erythritol, arabinose, Arabic gum and fructooligosaccharide in the single-ingredient formula promoted the growth of *Hafnia alvei*, but the growth promoting abilities of the black tea ferment prepared in Embodiment 1 and the soybean peptide powder were relatively remarkable. Moreover, the growth promoting ability of the complex formula was better than that of the 6 groups of single-ingredient formulas. In the 5 groups of complex-ingredient formulas, the complex-ingredient formula [5] (the black tea ferment prepared in Embodiment 1, the soybean peptide powder and Arabic gum in the weight ratio of 1:1:1) had the most remarkable ability on promoting the growth of *Hafnia alvei*, and the relative bacterial count of the complex-formula experimental group [5] was about 7.2 folds that of the control group.

Therefore, the prebiotic composition in certain proportion and specific variety could effectively and remarkably improve the growth ability of probiotics (like *Hafnia alvei*).

Embodiment 5-1: Influence of Specific Prebiotic Compositions in Different Proportions on *Hafnia alvei*

Herein, the specific prebiotic composition was obtained by combining the black tea ferment prepared in Embodiment 1, the soybean peptide powder (purchased from FUJI OIL Co. Ltd.), erythritol (purchased from SWEET TOWN ENTERPRISE CORP.) and Arabic gum (purchased from Buildmore Enterprise Co., Ltd.). The adopted liquid medium was the brain heart infusion broth (BHI, hereinafter referred to as the BHI medium, and purchased from Difco™). The adopted test strains were *Hafnia alvei* BCRC10906 purchased from Bioresource Collection and Research Center (BCRC). Each group is shown as Table 7.

The groups were divided into a control group and 3 experimental groups. The control group referred to a group without any prebiotics, and the experimental medium was 10 ml of the BHI medium. The experimental groups were an experimental group [1] to an experimental group [3] containing the black tea ferment prepared in Embodiment 1, the soybean peptide powder, erythritol and Arabic gum in different proportions. The experimental medium was 10 ml of the BHI medium containing 1 g of the prebiotic composition (namely a combination of about 0.38 g of the black tea ferment prepared in Embodiment 1, about 0.38 g of the soybean peptide powder, about 0.23 g of erythritol and about 0.02 g of Arabic gum, a combination of about 0.24 g of the black tea ferment prepared in Embodiment 1, about 0.24 g of the soybean peptide powder, about 0.48 g of erythritol and about 0.05 g of Arabic gum, and a combination of about 0.30 g of the black tea ferment prepared in Embodiment 1, about 0.30 g of the soybean peptide powder, about 0.36 g of erythritol and about 0.03 g of Arabic gum; and the 3 experimental groups are referred to as formulas [1] to [3]).

TABLE 7

| Group | Black tea ferment prepared in Embodiment 1:soybean peptide powder:erythritol:Arabic gum (weight ratio) |
|---|---|
| Control group | — |
| Experimental group [1] | Formula [1]-1:1:0.6:0.05 |
| Experimental group [2] | Formula [2]-1:1:2:0.2 |
| Experimental group [3] | Formula [3]-1:1:1.2:0.1 |

Firstly, 5% (v/v) of *Hafnia alvei* was inoculated to the BHI medium, and activated in an anaerobic operation box (5% of hydrogen, 10% of carbon dioxide and 85% of nitrogen) at 37° C. for 24 hours to obtain an experimental bacterial solution.

5% (v/v) of activated *Hafnia alvei* was added into each of test tubes filled with 10 mL of the experimental medium of each group respectively, and subjected to anaerobic culture at 37° C. for 24 hours; and double repeated experiments were carried out. Then, after culturing for 24 hours, the bacterial solution of each group was shaken up. 200 µl of the bacterial solution was charged into to a 96-well plate. $OD_{600nm}$ of each group was detected within 15 minutes through a disc-type full-spectrum optical quantometer (Brand: BioTek; Model: EPOCH). The absorbance of the control group was regarded as the relative bacterial count of 100±9.7%, and the relative bacterial count (%) of other groups was correspondingly converted. The detection result and the converted relative bacterial count result are shown in FIG. 4 and Table 8.

TABLE 8

| Group | Absorbance ($OD_{600}$) | Relative bacterial count (%) |
|---|---|---|
| Control group | 0.093 ± 0.009 | 100 ± 9.7 |
| Experimental group [1] | 0.487 ± 0.024 | 524 ± 25.8 |
| Experimental group [2] | 0.449 ± 0.035 | 483 ± 37.63 |
| Experimental group [3] | 0.545 ± 0.027 | 586 ± 29.03 |

As shown in FIG. 4, the $OD_{600nm}$ of the control group without any prebiotics was 0.093±0.009c. In the rest 3 experimental groups, the $OD_{600nm}$ of the experimental group [1] was 0.487±0.024b, the $OD_{600nm}$ of the experimental group [2] was 0.449±0.035b, and the $OD_{600nm}$ of the experimental group [3] was 0.545±0.027a. Therefore, the experimental groups [1] to [3] with different formulas promoted the growth of *Hafnia alvei*, but when the weight ratio of the black tea ferment prepared in Embodiment 1 to the soybean peptide powder to erythritol to Arabic gum was 1:1:1.2:0.1, the ability to promote the growth of *Hafnia alvei* was relatively remarkable, and the relative bacterial count was about 6 folds that of the control group.

Embodiment 5-2: Influence of Prebiotic Compositions in Specific Proportions on *Hafnia alvei*

The composing proportion of the prebiotic composition in Embodiment 5-1 was further adjusted. The specific proportion referred to that the prebiotic composition was obtained by combining the black tea ferment prepared in Embodiment 1, the soybean peptide powder (purchased from FUJI OIL Co. Ltd.), erythritol (purchased from SWEET TOWN ENTERPRISE CORP.) and Arabic gum (purchased from Buildmore Enterprise Co., Ltd.) according to a weight ratio of 3:3:3.6: 0.4. The adopted liquid medium was the brain heart infusion broth (BHI, hereinafter referred to as the BHI medium, and purchased from Difco™) The adopted test strains were *Hafnia alvei* BCRC10906 purchased from Bioresource Collection and Research Center (BCRC).

The groups were divided into a control group and an experimental group. The control group referred to a group without any prebiotics, and the experimental medium of the control group was 10 ml of the BHI medium. The experimental group referred to a group of a specific prebiotic composition, and the experimental medium of the experimental group was the BHI medium containing 10% (w/v) of the specific prebiotic composition (equivalent to that 10 ml of the BHI medium contained 1 g of the specific prebiotic composition). The specific prebiotic composition included 0.3 g of the black tea ferment prepared in Embodiment 1, 0.3 g of the soybean peptide powder, 0.36 g of erythritol and 0.04 g of Arabic gum.

5% (v/v) of *Hafnia alvei* was inoculated to the BHI medium, and activated in an anaerobic operation box (5% of hydrogen, 10% of carbon dioxide, and 85% of nitrogen) at 37° C. for 24 hours to obtain an experimental bacterial solution.

5% (v/v) of the activated *Hafnia alvei* was respectively inoculated to the experimental mediums of certain groups and subjected to anaerobic culture at 37° C. for 24 hours; and moreover, double repeated experiments were carried out.

After culturing for 24 hours, the bacterial solution was shaken up. 200 μl of the bacterial solution was charged into to a 96-well plate. $OD_{600nm}$ of each group was detected within 15 minutes through a disc-type full-spectrum optical quantometer (Brand: BioTek; Model: EPOCH).

Figure 5:
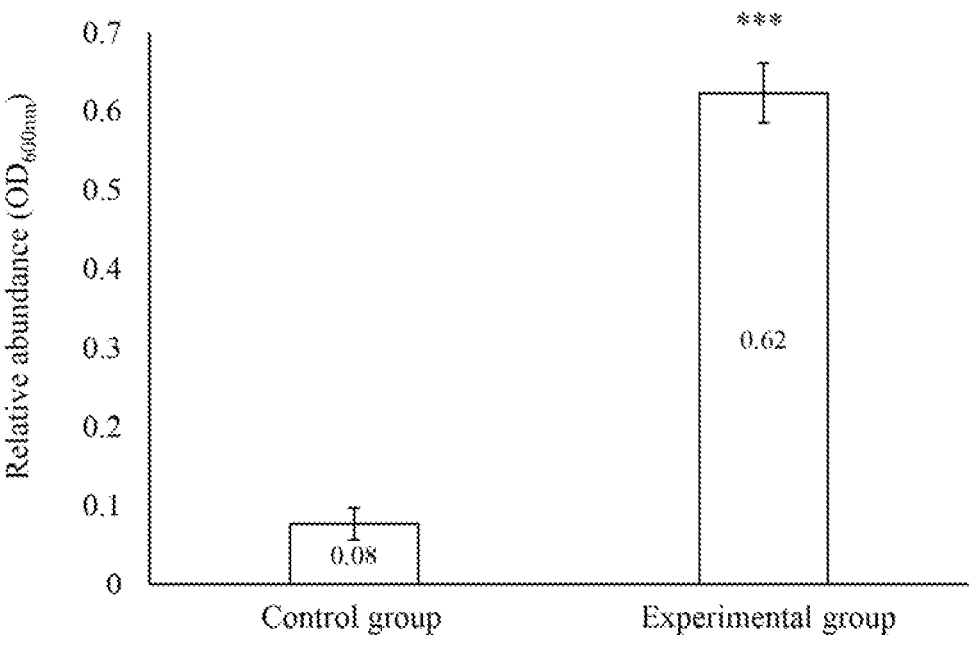
FIG. 5 is a diagram of a relative abundance experiment result of influence of specific prebiotic compositions on *Hafnia alvei;*

As shown in FIG. 5, the $OD_{600nm}$ of the control group without any prebiotics was 0.08, and the $OD_{600nm}$ of the experimental group was 0.62, which indicates that the relative abundance of *Hafnia alvei* of the experimental group was about 8 folds that of the control group. Therefore, the specific prebiotic composition had a relatively good ability of promoting the growth of *Hafnia alvei*.

Embodiment 6: Human Experiment

The experiment was conducted to further confirm the influence of the specific prebiotic composition on a human body. The prebiotic composition obtained by combining the black tea ferment prepared in Embodiment 1, the soybean peptide powder (purchased from FUJI OIL Co. Ltd.), erythritol (purchased from SWEET TOWN ENTERPRISE CORP.) and Arabic gum (purchased from Buildmore Enterprise Co., Ltd.) in a weight ratio of 3:3:3.6:0.4 was tested.

Capsules, each containing 500 mg of the prebiotic composition, were provided for 10 subjects. Each person took 1 capsule (2 capsules per day) before breakfast and dinner every day for 4 consecutive weeks. In other words, the daily dosage of the prebiotic composition for each person was 1,000 mg. Moreover, fecal sampling, questionnaire feedback, and body composition measurement were performed at the $0^{th}$ week (before administration) and the $4^{th}$ week (after administration).

The 10 subjects were males or females aged from 20 to 55 who were consciously uncontrollable in appetite or have body fat of more than 25%.

The fecal sampling was to collect feces of the subjects, and the feces were delivered to an outsourcing detection unit (BIOTOOLS) to measure NGS microflora of the subjects and analyze the content of the short-chain fatty acids (SCFAs) in the intestinal tracts of the subjects. The strain for current NGS microflora detection was *Hafnia alvei.*

The questionnaire feedback was to analyze the questionnaire result after investigating through an international approved Council on Nutrition Appetite Questionnaire (CNAQ). The body composition measurement included body weight, body fat rate, waist circumference, and the like.

Embodiment 6-1: Analysis on Abundance of *Hafnia alvei* in Intestinal Tracts of Subjects 10 subjects were subjected to fecal sampling before taking the capsules containing the prebiotic composition (i.e., the $0^{th}$ week) and after taking the capsules containing the prebiotic composition (i.e., the $4^{th}$ week) respectively, and BIOTOOLS was commissioned to perform NGS microflora analysis, with the result shown in FIG. 6.

Herein, the detected strain was *Hafnia alvei.*

Figure 6:
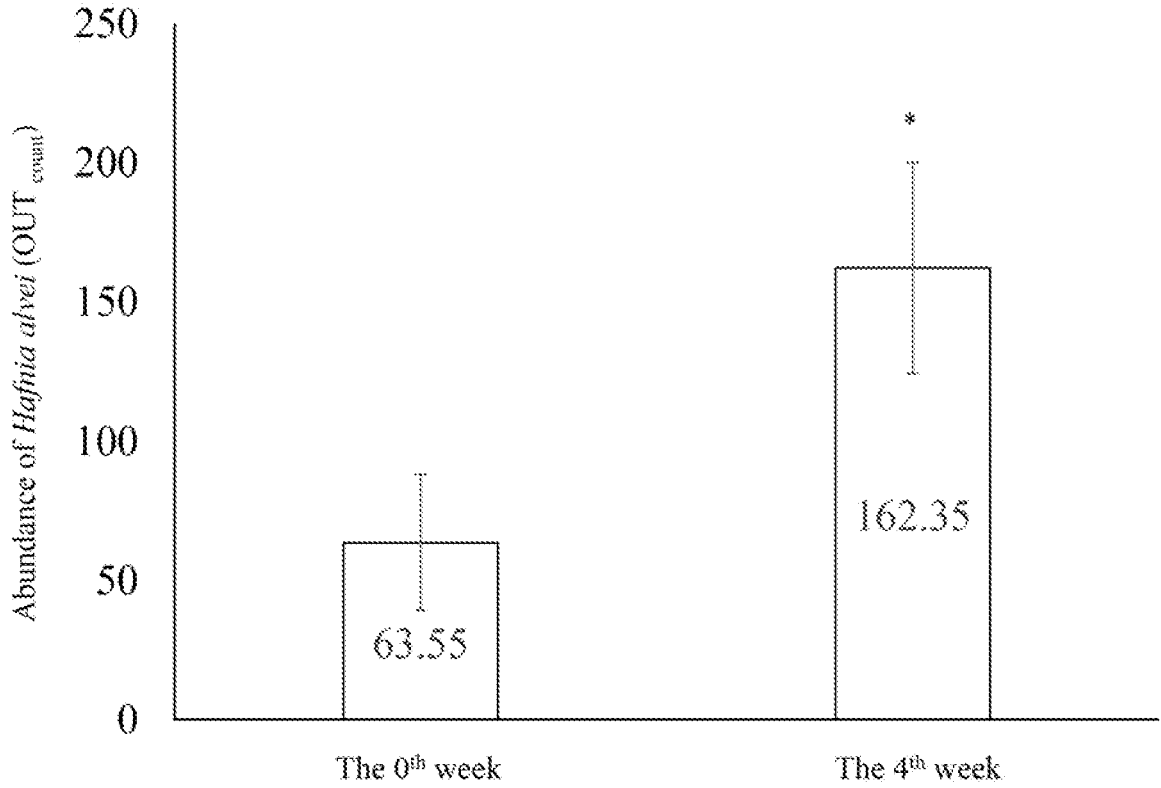
FIG. 6 is a diagram of an analysis result of average relative abundance of *Hafnia alvei* in intestinal tracts of subjects in the $0^{th}$ week and the $4^{th}$ week.

As shown in FIG. 6, the average abundance of *Hafnia alvei* of the 10 subjects at the $0^{th}$ week was 63.55 $OUT_{count}$, and the average abundance of *Hafnia alvei* at the $4^{th}$ week was increased to 162.35 $OUT_{count}$. That is, after the 10 subjects took the capsules containing the prebiotic composition in the morning and evening for 4 consecutive weeks, the abundance of *Hafnia alvei* in the intestinal tracts was increased by 2.55 folds. When the amount of *Hafnia alvei* in the intestinal tracts is increased, the appetite of the subjects can be controlled. Therefore, by taking the prebiotic composition including the black tea ferment, the soybean peptide powder, erythritol and Arabic gum, the amount of *Hafnia alvei* in the intestinal tracts of the users can be effectively increased, and thus the appetite of the users is controlled.

Embodiment 6-2: Analysis on Content of Short-Chain Fatty Acids (SCFAs) in Intestinal Tracts of Subjects 5 subjects were subjected to fecal sampling before taking the capsules containing the prebiotic composition (i.e., the $0^{th}$ week) and after taking the capsules containing the prebiotic composition (i.e., the 4 th week) respectively, and BIOTOOLS was commissioned to perform analysis on the content of short-chain fatty acids (SCFAs) in the intestinal tracts, with the result shown in FIG. 7.

Figure 7:
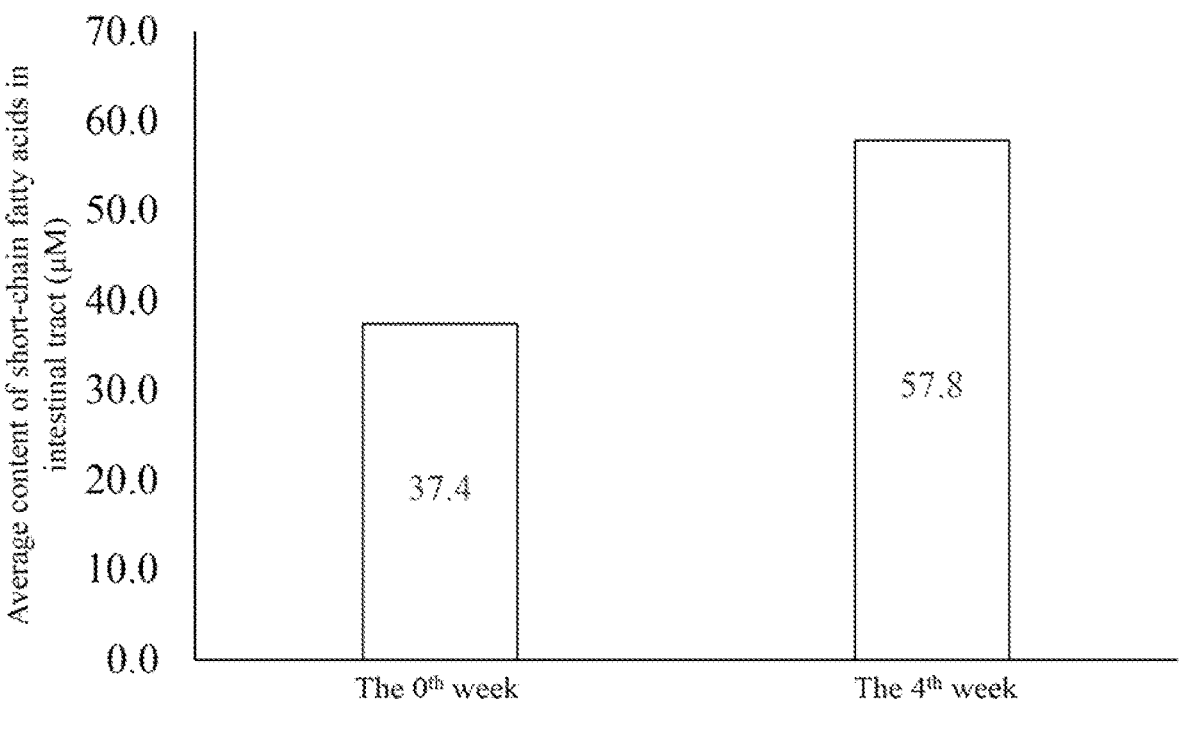
FIG. 7 is a diagram of an analysis result of average content of SCFAs in intestinal tracts of subjects in the $0^{th}$ week and the $4^{th}$ week.

As shown in FIG. 7, the average content of short-chain fatty acids in the intestinal tracts of the 5 subjects at the $0^{th}$ week was 37.4 μM, and the average content of short-chain fatty acids in the intestinal tracts at the $4^{th}$ week was increased to 57.8 μM. That is, after the 5 subjects continuously took the capsules containing the prebiotic composition in the morning and evening for 4 consecutive weeks, the content of short-chain fatty acid in intestinal tracts was increased by 1.55 folds. Moreover, the short-chain fatty acids in the intestinal tracts can be respectively combined with FFAR-2 and FFAR-3 subjects of intestinal cells, thereby promoting the secretion of satiety hormones PYY and GLP-1. In other words, when the content of short-chain fatty acids in the intestinal tracts is increased, the message conduction of the satiety hormones of the subjects will be facilitated, thereby controlling the appetite of the subjects. Therefore, by taking the prebiotic composition including the black tea ferment, the soybean peptide powder, erythritol and Arabic gum, the content of short-chain fatty acids in intestinal tracts of the users will be effectively increased, thereby helping the user to control the appetite.

Embodiment 6-3: Analysis of CNAQ of Subjects

The appetite of the 10 subjects was investigated with the CNAQ before taking the capsules containing the prebiotic composition (i.e., the $0^{th}$ week) and after taking the capsules containing the prebiotic composition (i.e., the $4^{th}$ week). Moreover, the questionnaire feedback results of the 10 subjects are shown in FIG. 8.

Figure 8:
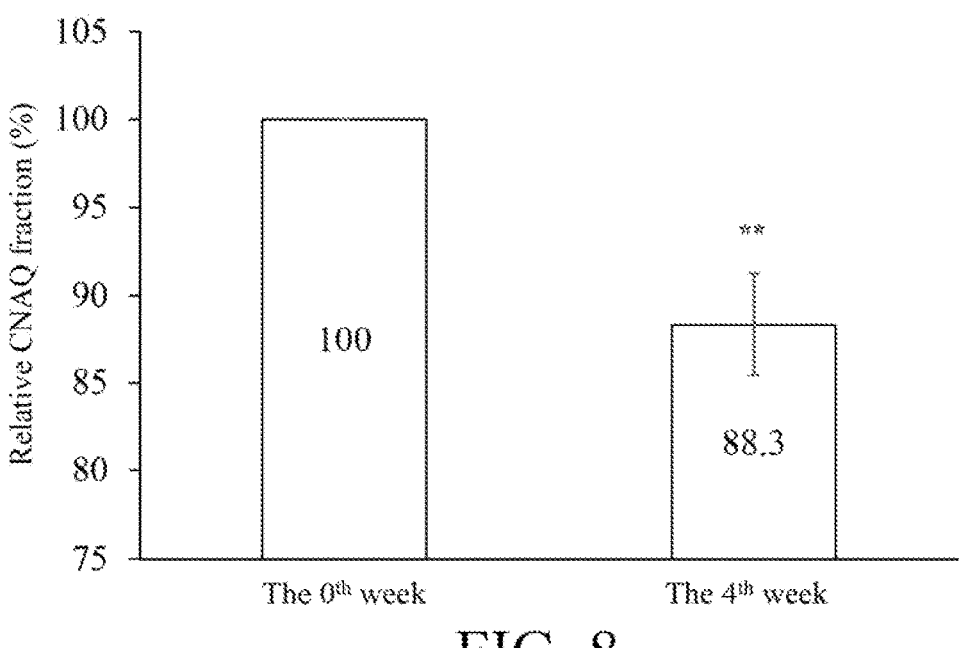
FIG. 8 is a diagram of an analysis result of an average relative CNAQ fraction of a subject in the $0^{th}$ week and the $4^{th}$ week.

As shown in FIG. 8, the average CNAQ fraction of the 10 subjects was regarded as 100%. After taking the capsules containing the prebiotic composition for 4 weeks, the average CNAQ fraction of the 10 subjects was reduced to 88.3%, which indicates that the appetite of the 10 subjects was reduced by 11.7%. Therefore, by taking the prebiotic composition composed of the black tea ferment, the soybean peptide powder, erythritol and Arabic gum, the appetite of the user will be effectively reduced, thereby achieving the effect of weight loss.

Embodiment 6-4: Analysis on Body Composition of Subjects

The body composition of the 10 subjects was measured by a body fat meter (Brand: TANITA BC-601FS) and a tape measure before taking the capsules containing the prebiotic composition (i.e., the $0^{th}$ week) and after taking the capsules containing the prebiotic composition (i.e., the $4^{th}$ week) respectively. In addition, the body composition results of the subjects are shown in FIG. 9 to FIG. 11.

Herein, the analyzed body composition items included body weight, body fat rate and waist circumference.

Figure 9:
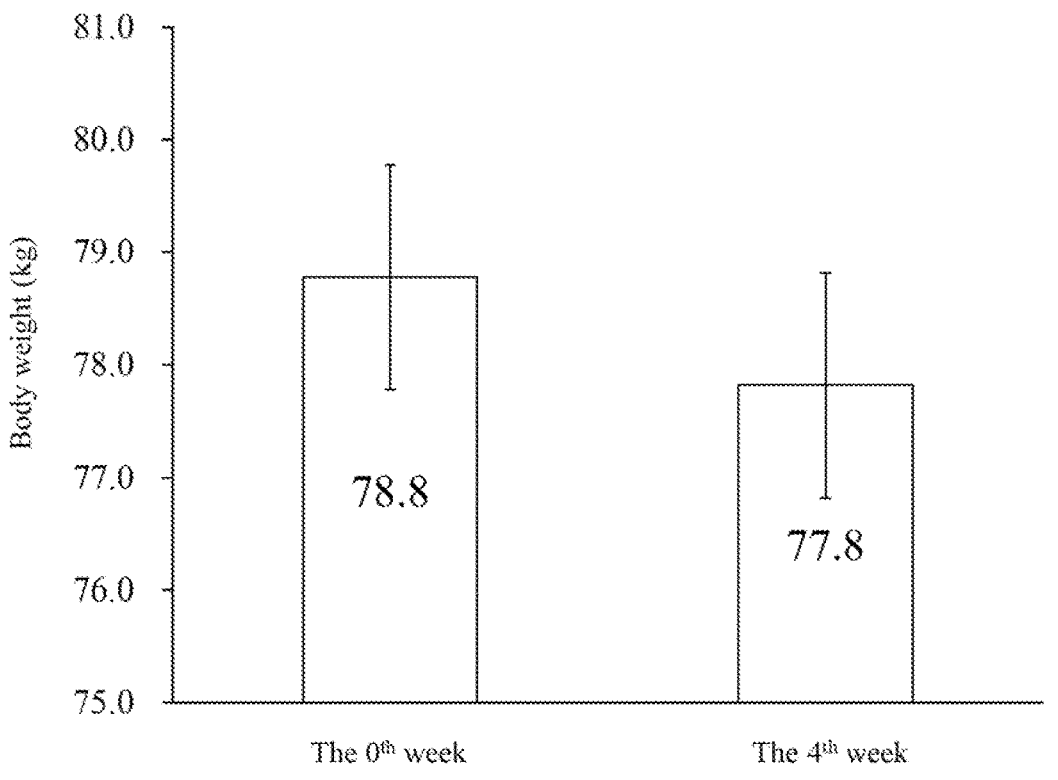
FIG. 9 is a diagram of an analysis result of average body weight of a subject in the $0^{th}$ week and the $4^{th}$ week.

As shown in FIG. 9, the average body weight of the 10 subjects was 78.8 kg before taking the capsules containing the prebiotic composition in the $0^{th}$ week. The average body weight of the 10 subjects was decreased to be 77.8 kg after taking the capsule for 4 weeks. In other words, the average body weight of the subjects was decreased by 1.0 kg after taking the capsules containing the prebiotic composition for 4 weeks. Therefore, the body weight of the subject can be effectively reduced by taking the prebiotic composition composed of the black tea ferment, the soybean peptide powder, erythritol and Arabic gum, thereby achieving the effect of weight loss.

Figure 10:
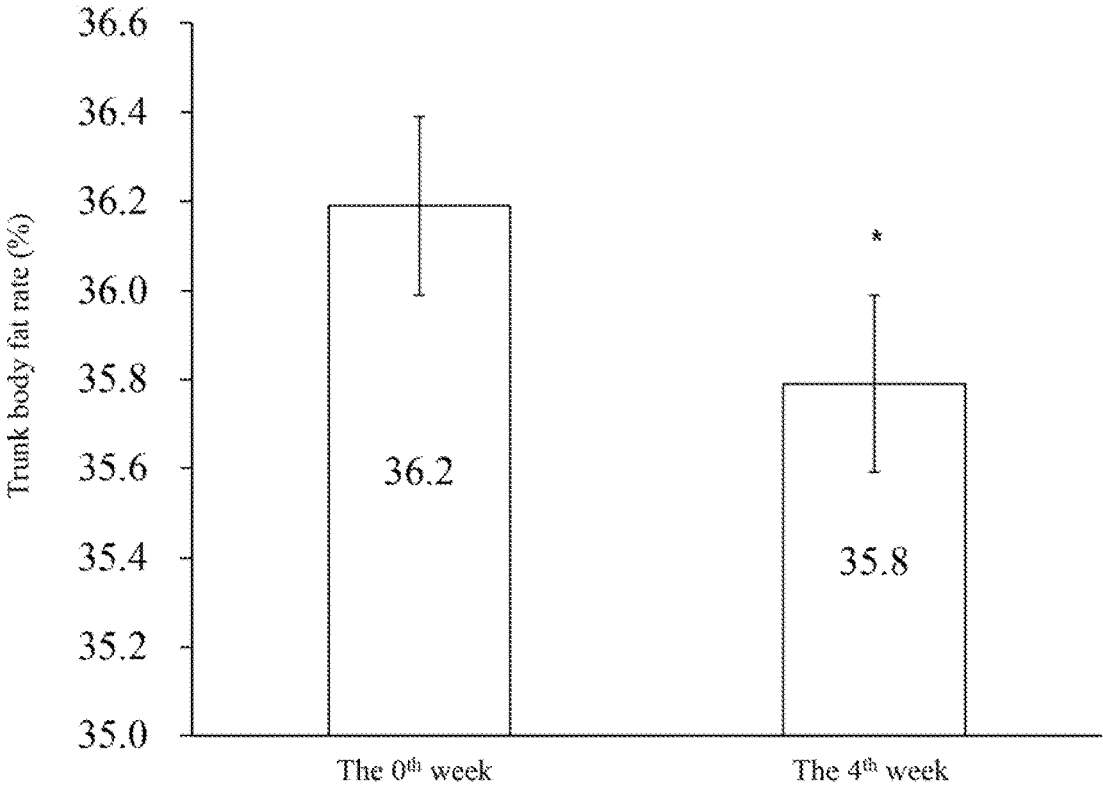
FIG. 10 is a diagram of an analysis result of average trunk body fat rate of a subject in the $0^{th}$ week and the $4^{th}$ week.
Figure 11:
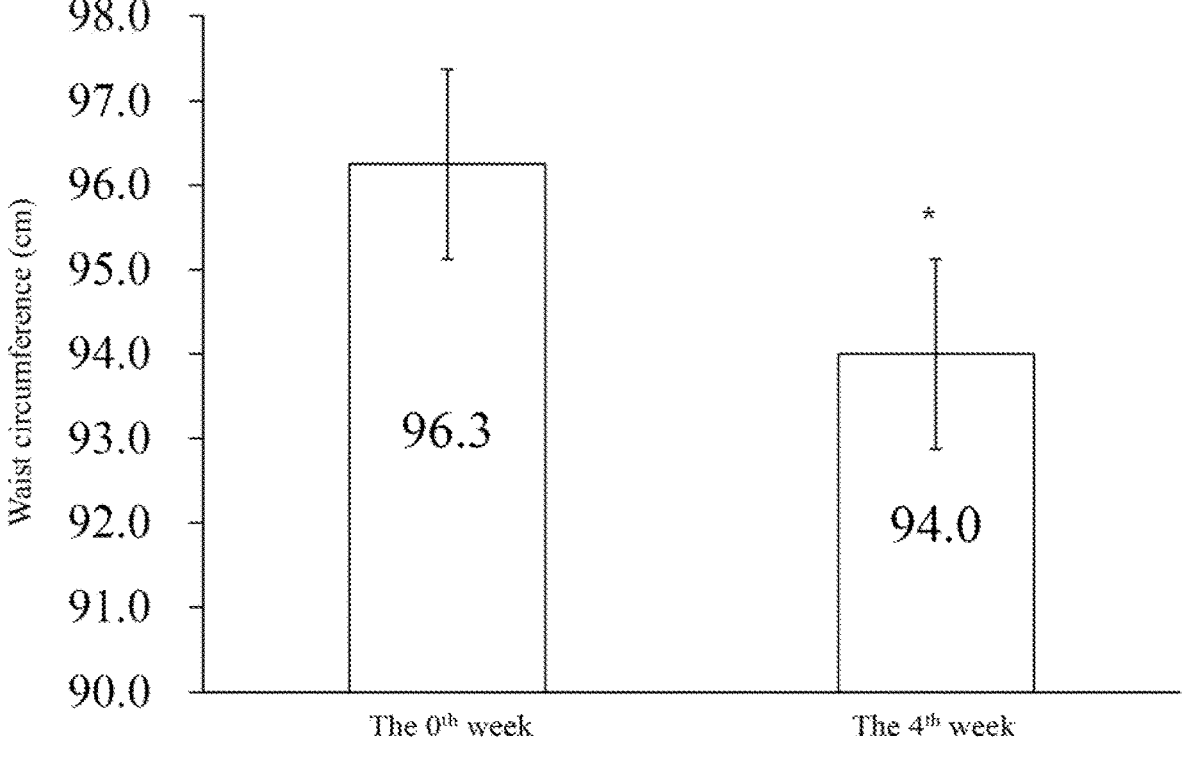
FIG. 11 is a diagram of an analysis result of average waist circumference of a subject in the $0^{th}$ week and the $4^{th}$ week.

As shown in FIG. 10, the average trunk body fat rate of the 10 subjects was 36.2% before taking the capsules containing the prebiotic composition in the $0^{th}$ week. The average trunk body fat rate of the 10 subjects was decreased to be 35.8% after taking the capsules for 4 weeks. In other words, the average trunk body fat rate of the subjects was decreased by 0.4% after taking the capsules containing the prebiotic composition for 4 weeks. Therefore, the trunk body fat rate of the subject can be effectively reduced by taking the prebiotic composition including the black tea ferment, the soybean peptide powder, erythritol and Arabic gum, thereby achieving the effect of weight loss.

As shown in FIG. 11, the average waist circumference of the 10 subjects was 96.3 cm before taking the capsules containing the prebiotic composition in the $0^{th}$ week. The average waist circumference of the 10 subjects was decreased to be 94.0 cm after taking the capsules for 4 weeks. In other words, the average waist circumference of the subjects was decreased by 2.3 cm after taking the capsules containing the prebiotic composition for 4 weeks. Therefore, the waist circumference of the subject can be effectively reduced by taking the prebiotic composition including the black tea ferment, the soybean peptide powder, erythritol and Arabic gum, thereby achieving the effect of weight loss.

In conclusion, the prebiotic composition containing the black tea ferment and the bioactive substance (such as the soybean peptide powder, the pea protein, the rice protein, the corn oligopeptide powder or the combination thereof) according to any embodiment of the present disclosure can be used for promoting the growth of *Hafnia alvei*, increasing the content of short-chain fatty acids in the intestinal tracts, inhibiting the appetite of the subjects, losing the weight of the subjects, reducing the body fat (such as trunk body fat) of the subjects and reducing the waist circumference of the subjects. Moreover, the prebiotic composition can be used for preparing the composition for weight loss and can also be used for controlling the appetite of the subjects.

Although the present disclosure has been described in considerable detail with reference to certain preferred embodiments thereof, the disclosure is not for limiting the scope of the invention. Persons having ordinary skill in the art may make various modifications and changes without departing from the scope and spirit of the disclosure. Therefore, the scope of the appended claims should not be limited to the description of the preferred embodiments described above.

What is claimed is:

1. A method for weight loss of a subject in need thereof, comprising: administering an effective dose of a prebiotic composition to the subject, the prebiotic composition comprising a black tea ferment and a bioactive substance, a weight ratio of the black tea ferment to the bioactive substance being 9:1 to 1:9, the bioactive substance being soybean peptide powder, pea protein, rice protein, corn oligopeptide powder, or a combination thereof, and the black tea ferment being prepared by the following steps:
    extracting tea leaves of *Camellia sinensis* with water at 50° C. to 100° C. for 0.5 hours to 3 hours to obtain a black tea extract; and
    fermenting the black tea extract with *Saccharomyces cerevisiae* BCRC20271, *Bifidobacterium lactis* BCRC 910887, *Lactobacillus gasseri* BCRC910886, and *Gluconacetobacter xylinus* BCRC12335 for 12 days to 25 days to obtain the black tea ferment;
    wherein the effect of weight loss is achieved by promoting growth of *Hafnia alvei* in the intestinal tract of the subject.

2. The method according to claim 1, wherein the prebiotic composition further comprises erythritol, Arabic gum, or a combination thereof.

3. The method according to claim 2, wherein a weight ratio of the black tea ferment to the bioactive substance to erythritol or Arabic gum is 1:1:0.05-2.

4. The method according to claim 2, wherein a weight ratio of the black tea ferment to the bioactive substance to erythritol to Arabic gum is 3:3:3.6:0.4.

5. The method according to claim 1, wherein the bioactive substance is the soybean peptide powder.

6. The method according to claim 1, wherein the prebiotic composition has an ability to increase the content of short-chain fatty acids in intestinal tracts.

7. The method according to claim 1, wherein the prebiotic composition has an ability to inhibit appetite of the subject.

8. The method according to claim 1, wherein the prebiotic composition has an ability to lose weight, and reduce body fat and waist circumference of the subject.

9. The method according to claim 8, wherein the body fat is trunk body fat.

10. The method according to claim 1, wherein the effective dose of the prebiotic composition is 500 g.

11. The method according to claim 10, wherein the prebiotic composition is administered twice a day.

\* \* \* \* \*